United States Patent [19]
Osterlind

[11] Patent Number: 5,879,331
[45] Date of Patent: Mar. 9, 1999

[54] MEDICAL DEVICES HAVING NEEDLE RETRACTION AND NEEDLE BIASING MECHANISM

[75] Inventor: Roland J. Osterlind, Hoeganaes, Sweden

[73] Assignee: Ohmeda Inc, Liberty Corner, N.J.

[21] Appl. No.: 857,926

[22] Filed: May 16, 1997

[30] Foreign Application Priority Data

May 22, 1996 [GB] United Kingdom .................. 9610682

[51] Int. Cl.⁶ ...................................................... A61M 5/00

[52] U.S. Cl. ............................................ 604/110; 604/192

[58] Field of Search ..................... 604/110, 111, 604/195, 197, 198, 192

[56] References Cited

U.S. PATENT DOCUMENTS

| 5,232,456 | 8/1993 | Gonzalez | 604/198 |
|---|---|---|---|
| 5,447,501 | 9/1995 | Karlsson et al. | 604/198 |
| 5,545,146 | 8/1996 | Ishak | 604/198 |

*Primary Examiner*—Michael Buiz
*Assistant Examiner*—Julian W. Woo
*Attorney, Agent, or Firm*—Roger M. Rathbun; Eric M. Lee

[57] ABSTRACT

A medical device includes a hollow needle having a distal tip for piercing the skin of a patient. A housing is provided for moving the needle relative to said housing between a first ready-for-use position and a second retracted needle protected position. A resilient arm is attached to the housing, said arm having a free end which in the second retracted needle protected position of the needle, engages said needle to move said distal tip laterally.

2 Claims, 2 Drawing Sheets

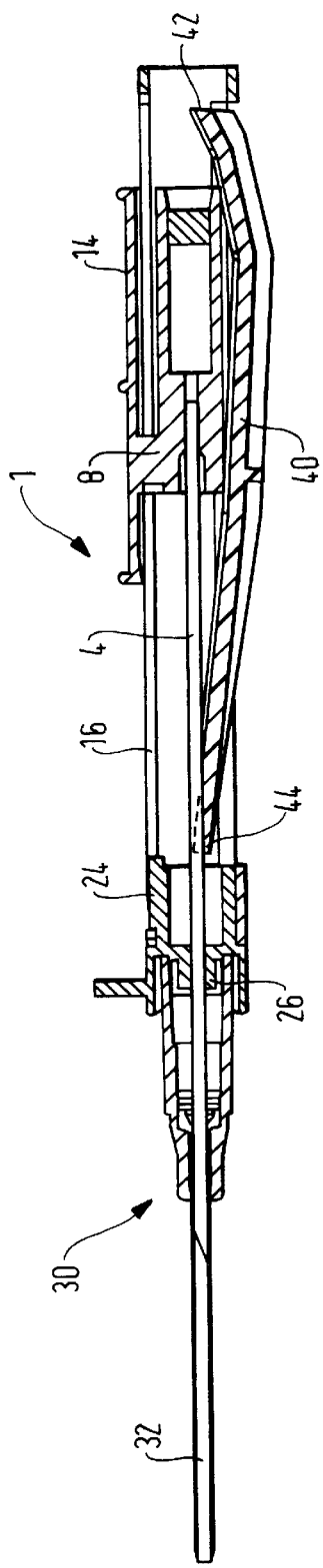
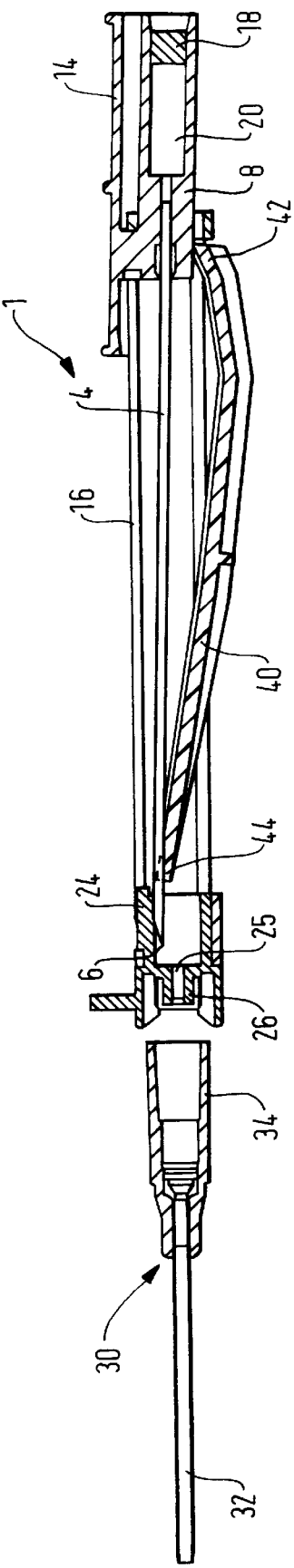

MEDICAL DEVICES HAVING NEEDLE RETRACTION AND NEEDLE BIASING MECHANISM

BACKGROUND OF THE INVENTION

The present invention relates to medical devices and, in particular, to medical devices such as intravenous catheters which include a hollow needle having a sharp distal end or tip for piercing the skin of a patient.

The existence of infectious diseases such as AIDS and hepatitis has highlighted the danger to which medical personnel may be exposed when treating patients by means of catheter devices where a sharp needle tip is used to pierce the skin of a patient. Medical personnel have been infected by physical contact with, or accidental prick by an infected needle (needle-stick).

In order to protect medical personnel against inadvertent needle-stick, a number of solutions have been developed whereby a protective means incorporated within the catheter prevents physical contact with the needle after use and hence against inadvertent needle-stick.

One known device for protecting the needle after use is described in U.S. Pat. No. 5,447,501. In this document, there is described an infusion catheter assembly including a hollow needle having a sharpened distal tip for piercing the skin of a patient. In a ready-for-use position the needle passes through a hole in a rigid front part which houses a resilient member. The resilient member is retained under tension by the needle flank and exerts a force substantially at right angles to the longitudinal direction of the needle. In its retracted position, that is, when the needle tip is moved back through and beyond the hole in the rigid front part the resilient member biases the needle tip laterally to prevent reentry of the needle tip through the hole.

This device is a relatively simple and economic device and is effective to minimize the danger of inadvertent needle stick.

However, since the resilient member is under compression until the device is actually used and since the shelf life of the device is up to three years from manufacture, it has been found advisable to make the resilient member of coiled spring steel in order to avoid the permanent set of the resilient member which would thereby lose its resilience.

It is an aim of the present invention to provide a simple but effective means for protecting the point of a needle forming part of a medical device which incorporates resilient means for deflecting a needle tip in a needle protected position but which avoids the necessity of using coiled spring steel.

BRIEF SUMMARY OF THE INVENTION

According to the present invention, a medical device comprises a hollow needle having a sharpened distal tip for piercing the skin of a patient, means for moving the needle relative to a housing between a first ready-for-use position and a second retracted needle protected position, the housing including a front part formed with a through hole for the passage therethrough of the needle and resilient means which in the second retracted needle protected position of the needle engages the needle to prevent the needle passing through the hole, in which the resilient means is in the form of a resilient arm attached to the housing, the resilient arm including a free end which in the second retracted needle protected position of the needle engages the needle flank to move said distal tip laterally, thereby to prevent distal tip from entering the hole.

Preferably, the resilient arm is made from plastic material.

BRIEF DESCRIPTION OF THE DRAWINGS

An embodiment of the invention will now be described, by way of example, reference being made to the figures of the accompanying diagrammatic drawings in which:

FIG. 3 is a longitudinal cross-section similar to FIG. 2, but illustrating the needle after use between its ready-for-use position and a needle protected position;

FIG. 4 is a cross-sectional similar to FIGS. 2 and 3, but showing the needle in its needle protected position and a cannula assembly separated from the remainder of the catheter assembly.

DETAILED DESCRIPTION OF THE PREFERRED EMBODIMENT

Figure 1:
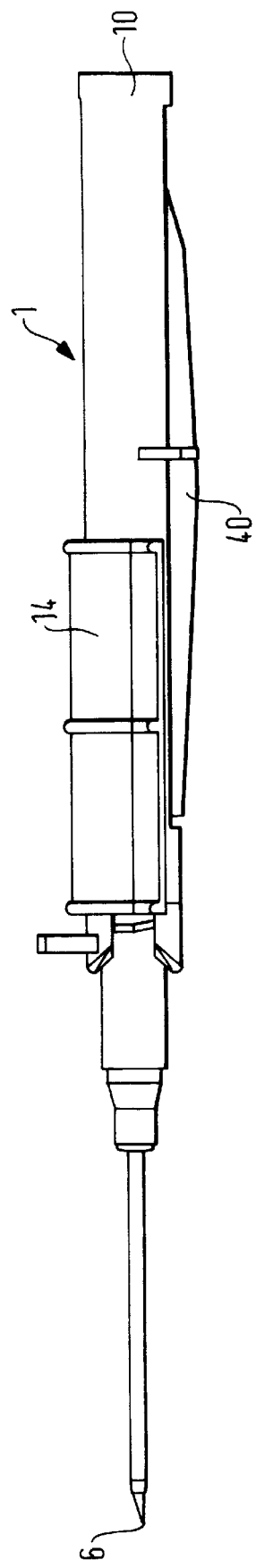
FIG. 1 is a side elevation of an infusion catheter assembly with its needle in a ready-for-penetration position.

As shown, an infusion catheter assembly 1 includes a needle assembly 2 comprising a hollow needle 4 having a sharpened distal tip 6, said needle 4 extending forwardly from a needle hub 8. The needle hub 8 is located for sliding movement within a housing 10 and includes a lug 12 supporting a gripper 14. The lug 12 extends through a slot 16 formed in the housing 10 in order that the gripper 14 can be engaged to reciprocate the needle hub 8 forwardly and rearwardly along the length of the housing 10. The needle hub 8 is hollow and is closed by a filter 18 which with the hub 8 defines a blood flashback chamber 20.

The forward distal end of the housing 10 is effectively closed by a hub support member 24 connected thereto. However, the member 24 is formed with a through hole 25 to allow the passage therethrough of the needle 4. The forward face of the member 24 is formed with a forwardly extending boss 26 for supporting the proximal end of a cannula assembly 30. As is well known in the art, the cannula assembly 30 comprises a hollow cannula 32 attached to a cannula hub 34.

According to the present invention, attached to the housing 10 is a resilient arm of plastic material 40, the arm 40 has a proximal end 42 and a distal end 44. As illustrated, the arm 40 is so shaped and mounted on the housing 10 that the ends 42, 44 tend to enter the interior of the housing 10.

Figure 2:
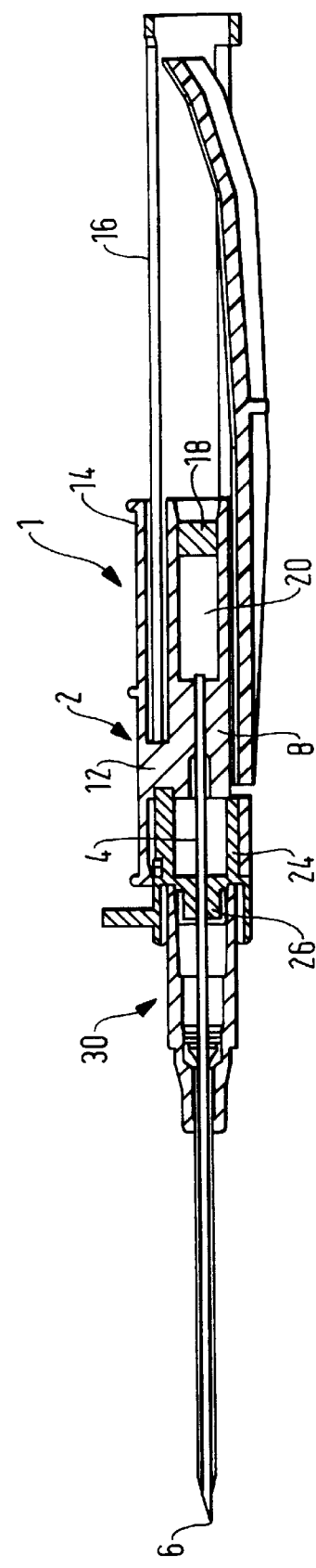
FIG. 2 is a longitudinal cross-section through the catheter assembly of FIG. 1.

In the ready-for-use position, as illustrated in FIGS. 1 and 2, the needle hub 8 is located at the forward end of the housing 10 such that the needle 4 extends through the hole 25 in the hub support member 24 and through the cannula assembly 30, so that the distal tip 6 of the needle 4 extends beyond the free distal end of the hollow cannula 32. In this position, the hub 8 engages the end 44 and thus causes the arm 40 to adopt the position as illustrated in FIG. 2 with the proximal end 42 of the arm located within the interior of the housing 10.

Once penetration of the patient's skin has been effected, the gripper 14 is engaged to move the needle hub 8 along and towards the proximal end of the housing 10, that is, towards the position illustrated in FIG. 3. This movement of the needle hub 8 will cause the needle 4 to be withdrawn through the hollow cannula 32 and the cannula hub 34. The proximal end of the needle hub 8 will also engage the arm 40 adjacent its proximal end 42 thereby forcing the distal end 44 of the arm to engage the flank of the needle 4.

This rearward movement of the needle hub 8 continues until it reaches the needle protected position as illustrated in FIG. 4.

In this position, the needle hub 8 will have caused the proximal end 42 of the arm 40 to move outwardly from the interior of the housing 10 and simultaneously cause the distal end 44 of the arm 40 to engage and move the needle laterally such that the needle tip 6 can no longer enter the through hole 25 in the hub support 24.

In this position the cannula assembly 30 can then be removed from the hub support 24.

A particular advantage of the embodiment described above is that the arm can be made of a resilient plastic material. Further, the distal end 44 of the arm will not initially apply any force to the needle 4 when starting the withdrawal of the needle through the cannula 32, the force on the needle 4 will only increase when the needle hub 8 is moved to the back of the housing 10 and the friction force will be a maximum just before the needle 4 reaches its needle protected position. This is important since the initial force of withdrawal of the needle 4 from the patient is very critical to the user, usually a nurse, and if it too high she will not get the right feel.

It is claimed:

1. A medical device comprising a hollow needle having a sharpened distal tip for piercing the skin of a patient, a housing having a means for moving said needle relative to said housing between a first ready-for-use position where said needle tip is external of said housing and a second retracted needle protected position where said needle tip is within said housing, said housing including a front part formed with a through hole for the passage therethrough of said needle and resilient means which in the second retracted needle protected position of said needle engages said needle to prevent said needle passing through said hole wherein said resilient means comprises a resilient arm attached to said housing, said resilient arm including a free end which in the second retracted needle protected position of said needle, engages said needle to move said distal tip laterally away from a longitudinal axis of said housing, thereby to prevent said distal tip from entering said hole.

2. A medical device as claimed in claim 1, in which said resilient arm is made from plastic material.

* * * * *